(12) United States Patent
Lemonds et al.

(10) Patent No.: US 7,456,313 B2
(45) Date of Patent: Nov. 25, 2008

(54) LIQUID-PHASE (AMM)OXIDATION PROCESS

(75) Inventors: Andrew Michael Lemonds, Schwenksville, PA (US); Donald Lee Zolotorofe, Ivyland, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 11/646,962

(22) Filed: Dec. 28, 2006

(65) Prior Publication Data

US 2007/0161812 A1 Jul. 12, 2007

Related U.S. Application Data

(60) Provisional application No. 60/757,764, filed on Jan. 10, 2006.

(51) Int. Cl.
*C07C 53/126* (2006.01)
(52) U.S. Cl. ............... 562/512; 562/546; 562/549; 502/241
(58) Field of Classification Search ........... 562/512, 562/546, 549; 502/241
See application file for complete search history.

(56) References Cited

U.S. PATENT DOCUMENTS

| | | | |
|---|---|---|---|
| 3,483,250 A | 12/1969 | Sugarman | |
| 3,624,147 A | 11/1971 | David et al. | |
| 4,379,925 A | 4/1983 | Grasselli et al. | |
| 4,900,480 A | 2/1990 | Litz et al. | |
| 6,147,256 A | 11/2000 | Costantini et al. | |
| 6,180,825 B1 * | 1/2001 | Lin et al. | 562/549 |
| 6,504,053 B1 | 1/2003 | Chaturvedi et al. | |
| 6,700,015 B2 | 3/2004 | Chaturvedi et al. | |
| 6,762,319 B1 * | 7/2004 | Fache et al. | 562/527 |
| 6,768,013 B1 * | 7/2004 | Pujado | 549/531 |
| 6,790,988 B2 | 9/2004 | Chaturvedi et al. | |
| 6,809,219 B2 * | 10/2004 | Han et al. | 562/549 |
| 6,825,380 B2 | 11/2004 | Chaturvedi et al. | |
| 6,965,046 B2 | 11/2005 | Paparizos et al. | |
| 2002/0151747 A1 | 10/2002 | Unruh et al. | |
| 2004/0092769 A1 | 5/2004 | Yunoki et al. | |
| 2004/0147777 A1 | 7/2004 | Fache et al. | |
| 2006/0159818 A1 | 7/2006 | Kunieda | |

FOREIGN PATENT DOCUMENTS

| | | |
|---|---|---|
| EP | 126488 | 11/1984 |
| EP | 145469 | 6/1985 |
| GB | 709 674 | 6/1954 |
| GB | 1 585 011 | 2/1981 |
| WO | WO 03/059856 | 7/2003 |
| WO | WO 03/099755 | 12/2003 |

OTHER PUBLICATIONS

Anonymous, "Examples of solubility parameters" Encyclopedia of Polymer Technology, pp. 1-4, Jul. 20, 1995.
John Burke, "Solubility Parameters; Theory and application: Part 2—The Hildebrand solubility parameter", internet article, pp. 1-5, Aug. 24, 2005.
Paul C. Sadek, "Internet article", Illustrated Pocket Dictionary of Chromatography, pp. 1-2, Jul. 15, 2004.

* cited by examiner

*Primary Examiner*—Daniel M Sullivan
*Assistant Examiner*—Sudhakar Katakam
(74) *Attorney, Agent, or Firm*—Kenneth Crimaldi

(57) ABSTRACT

A process for oxidizing a hydrocarbon, which comprises subjecting the hydrocarbon to a liquid phase catalytic oxidation reaction in the presence of at least one oxidation catalyst to form an oxidized product.

11 Claims, No Drawings

LIQUID-PHASE (AMM)OXIDATION PROCESS

This is a non-provisional application of prior pending U.S. provisional Application Ser. No. 60/757,764 filed on Jan. 10, 2006.

This invention relates to a process for the partial oxidation of hydrocarbons to oxidized products in non-polar liquid media.

Commercially, the current process for the manufacture of (meth)acrylic acid or (meth)acrylonitrile involves a two-step catalytic oxidation reaction starting with a propene or isobutene feed. Typically, the oxidation is performed in the gas phase, although there have been reports of liquid-phase oxidation of propene to acrylic acid. For example, Eur. Pat. Appl. No. 145,469 discloses the oxidation of propene to acrylic acid in water using a palladium-containing catalyst. However, alkanes are more readily available and cheaper starting materials than alkenes, and it would be desirable to oxidize alkanes directly to unsaturated carboxylic acids or nitriles in a liquid medium. It would also be desirable to have alternative catalytic methods for the oxidation of alkenes or other hydrocarbons to various oxidized products in a liquid medium.

The problem addressed by the present invention is to provide a liquid-phase method for the oxidation of hydrocarbons to oxidized products in a liquid medium.

STATEMENT OF INVENTION

The present invention provides a process for oxidizing a hydrocarbon, which comprises subjecting the hydrocarbon to a liquid phase catalytic oxidation reaction in the presence of at least one oxidation catalyst to form an oxidized product, wherein said liquid phase comprises a solvent having a boiling point of at least 25° C. and Hildebrand solubility parameter no greater than 7 $cal^{1/2}cm^{-3/2}$ (14 $MPa^{1/2}$).

DETAILED DESCRIPTION

Percentages are weight percentages, and temperatures are in ° C., unless specified otherwise. Boiling points are atmospheric-pressure boiling points. Solubilities are measured at 20° C. As used herein the term "(meth)acrylic" refers to acrylic or methacrylic.

In addition to the hydrocarbon, the feed components for the liquid-phase oxidation of a hydrocarbon may also include the corresponding alkanol which will dehydrate to the alkene under the reaction conditions. In one embodiment of the invention, the hydrocarbon is a $C_3$-$C_8$ hydrocarbon, alternatively an acyclic $C_3$-$C_8$ hydrocarbon, alternatively an acyclic $C_3$-$C_8$ alkane or alkene. Preferably, a $C_3$-$C_8$ acyclic alkane is a $C_3$-$C_4$ alkane, i.e., propane, isobutane or n-butane. The hydrocarbon may be introduced into the feed as a gas or a liquid, but more typically as a gas. An oxygen-containing gas also is present in the reaction. This may be oxygen, air, or any other oxygen-containing gas suitable for this reaction. The oxygen-containing gas may also contain nitrogen and other inert gases, including argon. The feed may also include water, which may be introduced as a gas or a liquid, but more typically as a gas. The water is not a solvent for the reaction. Preferably, the feed comprises from 0.5 to 90 mole % of the hydrocarbon, alternatively from 3 to 50 mole %.

An oxidized product is one containing oxygen, or containing additional unsaturation relative to the starting hydrocarbon. In one embodiment of the invention, the oxidized products are saturated and unsaturated carboxylic acids. In another embodiment, the oxidized product is an unsaturated aldehyde. In another embodiment, ammonia is present in the liquid phase catalytic oxidation reaction, and the oxidized product is an unsaturated nitrile; this oxidation is commonly referred to as an ammoxidation. The generic term "oxidation" herein is used to refer to any (amm)oxidation process, e.g., oxidation of hydrocarbons to unsaturated aldehydes or carboxylic acids, as well as oxidation of hydrocarbons in the presence of ammonia to produce unsaturated nitriles.

The liquid phase comprises at least one solvent, which may be a low molecular weight compound, an oil, or a polymeric material. Preferably, the solvent(s) is a non-polar solvent having less than 5% solubility in water, more preferably less than 3%, and most preferably less than 1%. The solvent(s) has a Hildebrand solubility parameter no greater than 7 $cal^{1/2}cm^{-3/2}$ (14 $MPa^{1/2}$), alternatively no greater than 6.5 $cal^{1/2}cm^{-3/2}$ (13 $MPa^{1/2}$), alternatively no greater than 6 $cal^{1/2}cm^{-3/2}$ (12 $MPa^{1/2}$). The Hildebrand solubility parameter, $\delta$, for a liquid is equal to the square root of the cohesive energy density, i.e., $\delta = \{(\Delta H - RT)/V_m\}^{1/2}$, where $\Delta H$ is the molar heat of vaporization, R is the gas constant, T is the absolute temperature, and $V_m$ is the molar volume. Hildebrand solubility parameters for solvents are readily available in the literature. Preferably, the solvent is stable towards oxidation under the reaction conditions, i.e., the amount of the solvent which oxidizes during the reaction is not detectable, or at least is not detrimental to product yield or purity. Stability towards oxidation also can be defined as having a redox potential greater than 3.5 eV, alternatively greater than 4.0 eV, alternatively greater than 4.5 eV, where the redox potential is computed for the loss of an electron and is relative to the standard hydrogen electrode half-reaction in acetonitrile. Redox potentials, E°, can be measured experimentally by well-known techniques, or calculated from free energies, $\Delta G$, using the equation $E° = \Delta G/F - K$, where F is the Faraday constant and K depends on the choice of reference electrode (K=4.43 eV for the hydrogen electrode). Free energies can be derived from quantum chemical calculations, see, e.g., Baik et al., *J Phys. Chem. A*, 2002, 106, 7407-7412; Fu et al., *J. Am. Chem. Soc.*, 2005, 127, 7227-7234. Calculation using such methods gives redox potentials of about 5 eV for perfluorocarbons.

In one embodiment of the invention, the liquid phase comprises at least one fluorinated organic compound, preferably a perfluorocarbon. Perfluorocarbons are substantially completely fluorinated, but may have residual traces of compounds having carbon-hydrogen bonds. Preferred perfluorocarbons include, e.g., perfluoro-ethers and -polyethers and $C_4$-$C_{18}$ perfluoroalkanes. Other preferred solvents may include, e.g., selected silicones or siloxanes and silicone or siloxane polymers; and hydrophobic ionic liquids having the solubility and stability properties set forth herein.

The oxidation catalyst may be a liquid dissolved in the solvent or a solid which does not dissolve in the solvent.

For the oxidation of alkanes by the process of this invention, a mixed-metal oxide ("MMO") catalyst capable of oxidizing alkanes to unsaturated carboxylic acids or nitriles is suitable. The general formula for such catalysts is $A_aM_bN_cX_dZ_eO_f$, where A is at least one element selected from the group consisting of Mo and W; M is at least one element selected from the group consisting of V and Ce; N is at least one element selected from the group consisting of Te, Sb and Se; X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and Z, if present, is at least one element selected from the group consisting of Zn, Ga, Ir, Sm, Pd, Au, Ag, Cu, Sc, Y, Pr, Nd and Tb; and wherein, when a=1, b=0.01 to 1.0, c=0.01 to 1.0, d=0.01 to 1.0, e=0 to 0.1, and f is dependent on the oxidation state of the other elements. In one embodiment, the MMO is a promoted MMO, in which Z is present, preferably with a value of e from 0.001 to 0.1. Promoted MMO catalysts are described, e.g., in U.S. Pat. Nos. 6,825,380; 6,790,988; 6,700,015 and 6,504,053. In another embodiment, Z is absent (e=0), in which case the MMO catalyst has the formula $A_aM_bN_cX_dO_f$.

Preferably, when a=1, b=0.1 to 0.5, c=0.05 to 0.5, d=0.01 to 0.5 and e=0.001 to 0.02. More preferably, when a=1, b=0.15 to 0.45, c=0.05 to 0.45, d=0.01 to 0.2 and e=0 to 0.015. In one embodiment, e=0.005 to 0.1; preferably, e=0.005 to 0.1; more preferably, e=0.01 to 0.05. The value of f, i.e. the amount of oxygen present, is dependent on the oxidation state of the other elements in the catalyst. However, f is typically in the range of from 3 to 4.7. Preferably, A is Mo. Preferably, M is V. Preferably, N is Te or Sb. Preferably, X is Nb or Ta; and most preferably, X is Nb. In one embodiment of the invention, the catalyst is $Mo_aV_bTe_cNb_dZ_eO_f$. In one embodiment, Z is Pd.

The MMO catalyst is formed from an aqueous slurry or solution (preferably a solution) comprising solutions containing salts of the MMO component metals. Water is removed by any suitable method, known in the art, to form a catalyst precursor. Such methods include, without limitation, vacuum drying, freeze drying, spray drying, rotary evaporation and air drying. Conditions for drying MMO catalysts are known and may be found in U.S. Pat. Nos. 6,825,380; 6,790,988; 6,700,015 and 6,504,053.

Once obtained, the catalyst precursor is calcined. The calcination may be conducted in an oxygen-containing atmosphere or in the substantial absence of oxygen, e.g., in an inert atmosphere or in vacuo. The inert atmosphere may be any composition which is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 $hr^{-1}$.

The calcination is usually performed at a temperature of from 350° C. to 850° C., preferably from 400° C. to 700° C., more preferably from 500° C. to 640° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired mixed metal oxide.

In a preferred mode of operation, the catalyst precursor is calcined in two stages. In the first stage, the catalyst precursor is calcined in an oxidizing environment (e.g. air) at a temperature of from 200° C. to 400° C., preferably from 275° C. to 325° C. for from 15 minutes to 8 hours, preferably for from 1 to 3 hours. In the second stage, the material from the first stage is calcined in a non-oxidizing environment (e.g., an inert atmosphere) at a temperature of from 500° C. to 750° C., preferably for from 550° C. to 650° C., for 15 minutes to 8 hours, preferably for from 1 to 3 hours. Optionally, a reducing gas, such as, for example, ammonia or hydrogen, may be added during the second stage calcination.

In a particularly preferred mode of operation, the catalyst precursor in the first stage is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

Although any type of heating mechanism, e.g., a furnace, may be utilized during the calcination, it is preferred to conduct the calcination under a flow of the designated gaseous environment. Therefore, it is advantageous to conduct the calcination in a bed with continuous flow of the desired gas(es) through the bed of solid catalyst precursor particles.

The oxidation process of this invention may be carried out in a batch or continuous manner. Examples of suitable reactors include, e.g., agitated batch reactors, continuous stirred-tank reactors, plug-flow tubular reactors, slurry reactors and trickle-bed reactors. The reactor pressure may vary depending on the boiling points of the solvent and the reactants.

The oxidation is performed in a reactor in which the liquid phase either contains a soluble catalyst or is in contact with a solid heterogeneous catalyst. A gas phase may also be present since the feed gas may contain insoluble inerts or excess reactants, i.e. the reactor may be operated with or without a vapor head space. Most preferably the design will be such to prevent the occurrence of flammable conditions or detonation. Preferably, if a heterogeneous catalyst is employed, the catalyst is confined in a part of the reactor by a screen or other barrier which allows gas and liquid to pass through, but prevents the catalyst from leaving the reactor. In one embodiment of the invention, a heterogeneous catalyst is contained in a basket which is attached to an agitator shaft. In other embodiments, the catalyst is confined as a fixed bed or trickle bed. Alternatively, a slurry reactor can be utilized.

In one embodiment, the non-polar reaction solvent may be continuously withdrawn from the reactor and re-fed via a recycle stream. As the polar reaction products, including (meth)acrylic acid or nitrile and water, are produced, they will form a second liquid phase in the reactor. In some embodiments of the invention, a liquid-liquid phase separation may be effected within the reactor, for example in a quiescent zone, and the product removed as the separate polar liquid phase; optionally, it may be removed with the non-polar reaction solvent (i.e., as a two-phase liquid effluent).

The operating temperature for the reaction preferably is from 25° C. to 400° C. Preferably, the reaction temperature is at least 100° C., more preferably at least 150° C. Preferably, the reaction temperature is no more than 300° C., more preferably no more than 250° C. Preferably, the pressure in the reactor is at least atmospheric pressure (101 kPa absolute) and no more than 5000 psig (34,474 kPa). Preferably, the pressure is no more than 2000 psig (13,789 kPa), and more preferably no more than 500 psig (3,447 kPa). In one preferred embodiment, the reaction is carried out at lower pressure, i.e., no more than 250 psig (1,724 kPa), more preferably no more than 100 psig (689 kPa), and most preferably no more than 50 psig (345 kPa).

In one embodiment of the invention, material other than solvent is distilled from the reactor and condensed. Preferably, the condensate is separated from the noncondensables as separate liquid and gas process streams. In other embodiments of the invention, both solvent and aqueous product may be removed from the reactor. After a phase separation, if the solvent still contains entrained aqueous product, it can optionally be contacted with an extractant, preferably in a separator vessel, and the solvent can then be recycled to the reactor. Preferably, the extractant has very low solubility in the solvent, i.e., less than 10%, more preferably less than 5%, and most preferably less than 1%. Preferred extractants include polar solvents, e.g., water, acetic acid, formic acid, $C_1$-$C_5$ alcohols, tetrahydrofuran, $C_3$-$C_8$ ketones, $C_3$-$C_8$ esters, acetonitrile, formamide, N,N-dimethyl formamide, dimethyl sulfoxide, and mixtures thereof. Other preferred extractants include, e.g., hydrophilic ionic liquids; hydrophilic perfluorocarbons, e.g., trifluoroethanol, trifluoroacetic acid; and nonpolar solvents which have low solubilities in the reaction solvent, e.g., benzene, toluene and xylenes.

In one embodiment of the invention, the starting material is an acyclic alkene. In addition to the alkene, the feed components for this process may also include the corresponding alkane, alkyne and/or an alkanol which will dehydrate to the alkene under the reaction conditions. Preferably, the $C_3$-$C_8$ acyclic alkene is a $C_3$-$C_4$ alkene, i.e., propene, isobutene or n-butene. The alkene may be introduced as a gas or a liquid. Preferably, the feed comprises from 0.5% to 90% of the $C_3$-$C_8$ acyclic alkene. The alkene may be oxidized to an aldehyde, e.g., oxidation of propene to acrolein or isobutene to methacrolein, or, in the presence of ammonia, to a nitrile.

For the oxidation of alkenes by the process of this invention, a mixed-metal oxide ("MMO") catalyst that comprises at least one atom of a group VIB element (e.g., Cr, Mo, W, or Unh), at least one atom of a group VA element (e.g., N, P, As, Sb or Bi), and at least two group VIII atoms and is capable of catalyzing the production of (meth)acrolein. For example, the catalyst may contain more than one atom of the same group VIII element (e.g., group VIII atoms include Fe, Co, Ni, Ru, Rh, Pd, Os, Ir, Pt). In another embodiment, the catalyst comprises two group VIII atoms which are different elements. In a further embodiment, the catalyst comprises at least Fe, Co or Ni. Yet another embodiment of catalyst includes at least two different atoms selected from Fe, Co or Ni and compounds which are mixture thereof (e.g., FeCo, FeNi, CoFe, CoNi).

Commonly, the catalyst comprises at least one atom of a group VIB element (e.g., Cr, Mo, W, or Unh). In another embodiment the catalyst comprises at least Mo.

In one embodiment, the catalyst comprises at least one atom of a group VA element (e.g., N, P, As, Sb or Bi). Another embodiment of catalyst comprises Mo, Bi, Fe and at least one atom of Ni or Co.

The catalyst optionally includes at least one atom from any of the alkali metal elements of group IA (e.g., H, Li, Na, K, Rb, Cs, or Fr). The catalyst also optionally comprises one or more atoms of elements from groups including: IIIA (e.g., B, Al, Ga, In or Tl) with one embodiment having at least one of Al or Tl; IIIB including the elements of the lanthanide series and the actinide series (e.g., Sc, Y, La, Ac, Ce, Pr, Nd, Pm, Sm, Eu, Gd, Tb, Dy, Ho, Er, Tm, Yb, Lu, Th, Pa, U, Np, Pu, Am, Cm, Bk, Cf, Es, Fm, Md, No, or Lr) with one embodiment having Ce; VIIB (e.g., Mn, Tc, Re, or Uns); VIA (e.g., O, S, Se, Te, or Po) with one embodiment having Te; IVA (e.g., C, Si, Ge, Sn, or Pb) with one embodiment having at least one of Mn or Pb; VB (e.g., V, Nb, Ta, or Unp) with one embodiment having Nb; IVB (e.g., Ti, Zr, Hf, or Unq) with one embodiment having Ti; IIB (e.g., Zn, Cd, or Hg) with one embodiment having Zn.

In one embodiment, the catalyst has the general formula:

$$Mo_aBi_bFe_cA_dE_eO_x,$$

wherein O is oxygen; A is at least one element selected from among Ni and Co; E is at least an element selected among alkali metal elements or alkaline earth metal elements, Tl, P, Te, Sb, Sn, Ce, Pb, Nb, Mn, As, Zn, Si, B, Al, Ti, Zn and W; and wherein a, b, c, d, e and x are the relative atomic ratios of the respective elements Mo, Bi, Fe, A, E and O, where a is 12, b is 0.1-10, c is 0.1-20, d is 1-20, e is 0-30, and x is a positive numerical value determined by the oxidation state of the other elements.

EXAMPLES

Examples 1-5

Liquid-Phase Oxidation of Propane to Acrylic Acid in Perfluorocarbon Solvent Media The liquid-phase oxidation of propane to acrylic acid (AA) was performed in a perfluorocarbon solvent (Fluorinert™ FC-77, available from 3M Company) with a mixed-metal oxide propane oxidation catalyst. This solvent has good solubility characteristics for the dissolution of propane and oxygen. It is not miscible with water or aqueous compositions of AA and similar carboxylic acids. The catalyst used in this experiment was a heterogeneous catalyst initially designed for gas phase oxidations (U.S. Pat. No. 6,180,825); it was an oxide of $MoV_{0.3}Te_{0.23}Nb_{0.17}Pd_{0.01}$, and it did not dissolve in the perfluorocarbon solvent.

The reaction was carried out in a continuous flow, stirred-tank reactor capable of pressurized operation. The free reactor volume of approximately 90 cc was completely filled with the perfluorocarbon solvent; i.e., no gaseous head space was present. About 30 cc of the catalyst was contained within an annular cylindrical "basket" with sidewalls fabricated of stainless steel mesh, which allowed the perfluorocarbon solvent to contact the catalyst. The catalyst basket was affixed to the agitator shaft and rotated during the reaction to provide mixing and distribution of the feed gas bubbles in the perfluorocarbon solvent.

To conduct the reaction, the reactor was heated to between 150 and 190° C. by an external, electrical heating mantle. The operating temperature was never allowed to exceed 190° C. Reactor pressure, controlled by a back-pressure regulator installed in the effluent line, was set at between 150 and 250 psig (1034 and 1724 kPa). Under these conditions, the reactor contents were below their ambient boiling point. Pressure was increased in conjunction with temperature increases to suppress boiling of the perfluorocarbon solvent and the reactor contents (AA, $H_2O$, etc.). Propane, oxygen, and nitrogen were bubbled via a dip tube into the reactor as a non-flammable mixture comprising 1.75% $C_3H_8$, 8.00% $O_2$, and 90.25% $N_2$ on a mole basis at a flow rate between 5 and 100 standard cubic centimeters per minute (sccm).

The reactor's liquid contents (predominantly the solvent) were continuously recirculated (10.5 cm³/min) through an external cooler and phase separator. An effluent heat exchanger was installed between the reactor and the pressure regulator. The cooled effluent was passed through a gas/liquid splitter, which directed a portion of the gas to a gas chromatograph for compositional analysis and the balance to exhaust. The liquid was directed to a gravity phase separator, where the upper aqueous phase accumulated for analysis and the lower reclaimed perfluorocarbon solvent phase was returned to the reactor.

Acrylic acid was produced in all cases examined under the operating conditions described above. Performance data are shown in Table 1 for operation at 150 and 190° C. and for a range of propane conversions, which were changed by varying the feed gas flow rate. All data points had carbon accountabilities of 100±3%.

Propane conversion (X), acrylic acid selectivity (S), and acrylic acid yield (Y) were calculated as follows:

$$X = 100 \times \left( \frac{\frac{1}{3} \text{ moles CO} + \frac{1}{3} \text{ moles CO}_2 + \text{moles C}_3\text{H}_6 + \frac{2}{3} \text{ moles HAc} + \text{moles PA} + \text{moles AA produced}}{\text{moles C}_3\text{H}_8 \text{ fed}} \right)$$

(HAc = acetic acid; PA = propionic acid; AA = acrylic acid)

$$S = 100 * \left( \frac{Y}{X} \right)$$

$$Y = 100 * \left( \frac{\text{moles AA produced}}{\text{moles C}_3\text{H}_8 \text{ fed}} \right)$$

TABLE 1

Performance data for Examples 1–5

| Ex. | T (°C.) | Gas Feed Flow Rate (sccm) | P, gauge psig (kPa) | X (%) | S (%) | Y (%) | r (mg/hr) |
|---|---|---|---|---|---|---|---|
| 1 | 150 | 94.2 | 179 (1234) | 7.6 | 25.0 | 1.9 | 6.1 |
| 2 | 150 | 46.7 | 163 (1124) | 11.0 | 32.8 | 3.6 | 5.7 |
| 3 | 150 | 22.7 | 163 (1124) | 19.1 | 37.7 | 7.2 | 5.5 |
| 4 | 190 | 94.2 | 222 (1531) | 19.9 | 40.3 | 8.0 | 25.5 |
| 5 | 190 | 46.7 | 228 (1572) | 27.1 | 41.1 | 11.1 | 17.5 |

X = propane conversion;
S = AA selectivity;
Y = AA yield;
r = rate of AA formation Examples 6-9

Liquid-Phase Oxidation of Propane to Acrylic Acid in Perfluorocarbon Polymer Oil Media With the use of an alternative liquid reaction medium having a negligible vapor pressure, the process used for Examples 1-5 may be operated at a substantially lower pressure. Moreover, if the pressure is lowered sufficiently, the non-perfluorocarbon species in the reactor will exit the reactor as a gas rather than a liquid.

Fomblin® PFPE Y LVAC 06/6 (available from Solvay-Solexis Inc.), a perfluoropolyether oil with similar chemical properties as the perfluorocarbon solvent used in Examples 1-5, was substituted as the liquid reaction medium. The process was investigated at 190° C. and between 15 and 150 psig (103 and 1034 kPa gauge, respectively). In this case, a feed gas comprising 7.00% $C_3H_8$, 14.00% $O_2$, and 79.00% $N_2$ on a mole basis was employed. Feed gas flow rates that varied between 10 and 100 seem were used. Acrylic acid formation was observed for conditions tested within these ranges.

Performance at constant temperature (190° C.) and feed rate (10.9 sccm) was examined as a function of pressure, and marked improvements in AA selectivity were observed as the pressure was reduced (Table 2). In these experiments, the Fomblin® was found to contain some entrained aqueous AA, which was extracted by washing the Fomblin® with water. The extracted AA was factored into the material balance. Since the Fomblin® was recycled, it is possible that some of the returned entrained AA was oxidized. Furthermore, this complication may be responsible for poorer carbon accountabilities, which were 100±10% for these experiments.

TABLE 2

Performance data for Examples 6–9

| Example | T (°C.) | P, gauge psig (kPa) | X (%) | S (%) | Y (%) | r (mg/hr) |
|---|---|---|---|---|---|---|
| 6* | 190 | 150 (1034) | 32.6 | 17.7 | 5.77 | 8.49 |
| 7 | 190 | 65 (448) | 42.3 | 21.3 | 9.01 | 13.3 |
| 8 | 190 | 35 (241) | 28.9 | 33.9 | 9.80 | 14.4 |
| 9 | 190 | 15 (103) | 33.0 | 45.2 | 14.91 | 21.9 |

X = propane conversion;
S = AA selectivity;
Y = AA yield;
r = rate of AA formation
*Carbon accountability for experiment no. 6 was 72%

Example 10

Liquid-Phase Oxidation of Propane to Acrylic Acid without Recycle of the Liquid Reaction Medium The process used in Examples 1-5 may also be operated without circulating the reactor contents through the phase separator. In order to achieve this mode of operation, a quiescent zone must be maintained towards the top of the reactor so that a liquid-liquid phase separation can be effected within the reactor itself. Preferably, in the case of a monomer oxidation product, this quiescent zone is also cooled and the size of the aqueous phase is minimized. In this scenario, only the upper aqueous phase exits the reactor, obviating the need for the liquid reaction medium to be recovered and recycled. In other words, the medium never leaves the reactor.

The process used in Examples 6-9 may also be operated without circulating the reactor contents through the phase separator. In order to achieve this mode of operation, the pressure must be maintained at a point that allows boiling of the aqueous product phase but not of the perfluorocarbon reaction medium. Furthermore, the reactor is not completely filled by the reaction medium, and a small head space is maintained in the reactor. In this scenario, only gas from the head space exits the reactor, obviating the need for the liquid reaction medium to be recovered and recycled. In other words, the medium never leaves the reactor.

Example 11

Liquid-Phase Oxidation of Propane to Acrylic Acid with Increased Feed Concentration The absorption of propane and oxygen into the perfluorinated liquids used in the prior examples generally obeys Henry's Law; the solute concentration in the liquid is proportional to the concentration of that species in the contacting gas phase. Furthermore, the propane oxidation reaction rate is a function of the dissolved propane concentration; thus to increase the reactor productivity, one can increase the concentration of these reactants in the liquid reaction medium.

The steady-state propane and oxygen concentrations in the gas bubbles within the reactor and in the exit gas increase with the feed gas flow rate. As more is fed, their concentration levels approach that of the feed gas, since the conversion decreases as the feed rate increases. This relationship between feed rate and conversion was observed in our experiments. It is not always practical, however, to operate at a low conversion. Another means of increasing the propane and oxygen concentrations in the perfluorocarbon liquids, hence further improving the process, is to employ a feed gas with higher reactant concentrations. It is more preferable, for example, to use a feed composing 7.00% $C_3H_8$ and 14.00% $O_2$ on a mole basis than a feed composing 1.75% $C_3H_8$ and 8.00% $O_2$.

The invention claimed is:

1. A process for oxidizing a hydrocarbon, which comprises subjecting the hydrocarbon to a liquid phase catalytic oxidation reaction in the presence of at least one oxidation catalyst to form an oxidized product, wherein said liquid phase comprises a solvent having a boiling point of at least 25° C. and Hildebrand solubility parameter no greater than 7 $cal^{1/2}$ $cm^{-3/2}$ (14 $MPa^{1/2}$); wherein said at least one oxidation catalyst is selected from the group consisting of:

(i) a mixed metal oxide having the empirical formula $$A_aM_bN_cX_dZ_eO_f$$

wherein A is at least one element selected from the group consisting of Mo and W; M is at least one element selected from the group consisting of V and Ce; N is at least one element selected from the group consisting of Te, Sb and Se; X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and Z is at least one element selected from the group consisting of Zn, Ga, Ir, Sm, Pd, Au, Ag, Cu, Sc, Y, Pr, Nd and Tb; and wherein, when a=1, b=0.01 to 1.0, c=0.01 to 1.0, d=0.01 to 1.0, e=0 to 0.1, and f is dependent on the oxidation state of the other elements; and (ii) a mixed metal oxide having the empirical formula $$Mo_aBi_bFe_cA_dE_eO_x,$$

wherein O is oxygen; A is at least one element selected from among Ni and Co; E is at least an element selected among alkali metal elements or alkaline earth metal elements, Tl, P, Te, Sb, Sn, Pb, Nb, Mn, As, Zn, Si, B, Al, Ti, Zn and W; and wherein a, b, c, d, e and x are the relative atomic ratios of the respective elements Mo, Bi, Fe, A, E and O, where a is 12, b is 0.1-10, c is 0.1-20, d is 1-20, e is 0-30, and x is a positive numerical value determined by the oxidation state of the other elements; and wherein temperature of the reaction is at least 100° C. and no more than 250° C.

2. The process of claim 1 in which the oxidation catalyst is a mixed metal oxide having the empirical formula $$A_aM_bN_cX_dZ_eO_f$$

wherein A is at least one element selected from the group consisting of Mo and W; M is at least one element selected from the group consisting of V and Ce; N is at least one element selected from the group consisting of Te, Sb and Se; X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and Z is at least one element selected from the group consisting of Zn, Ga, Ir, Sm, Pd, Au, Ag, Cu, Sc, Y, Pr, Nd and Tb; and wherein, when a=1, b=0.01, to 1.0, c=0.01 to 1.0, d=0.01 to 1.0, e=0 to 0.1, and f is dependent on the oxidation state of the other elements.

3. The process of claim 2 in which the hydrocarbon is an acyclic $C_3$-$C_8$ alkane and the oxidized product is an unsaturated carboxylic acid.

4. The process of claim 1 in which the solvent has a Hildebrand solubility parameter no greater than 6 $cal^{1/2}cm^{-3/2}$ (12 $MPa^{1/2}$).

5. The process of claim 4 in which the solvent is a perfluoroalkane, perfluoro-polyether or perfluoroether.

6. The process of claim 1 in which oxidized product is recovered from the solvent after a phase separation.

7. The process of claim 6 in which additional oxidized product is separated from the solvent as a solution in an extractant; said extractant having less than 1% solubility in the solvent.

8. The process of claim 3 in which the oxidation catalyst is $Mo_aV_bTe_cNb_dZ_eO_f$.

9. The process of claim 8 in which the solvent is a perfluoroalkane, perfluoro-polyether or perfluoroether.

10. The process of claim 9 in which temperature of the reaction is at least 150° C.

11. The process of claim 10 in which the hydrocarbon is propane, isobutane or n-butane.

* * * * *